（12） United States Patent
Nelson et al.

(10) Patent No.: US 7,074,195 B2
(45) Date of Patent: Jul. 11, 2006

(54) REAL-TIME, SOUND-QUALITY-COMPETITIVE, SINGLE-SITE FROM PLURAL-SITE, ANATOMICAL AUDIO SIGNAL SELECTION

(75) Inventors: Alex T. Nelson, Portland, OR (US); Jim T. Belesiu, Lake Oswego, OR (US)

(73) Assignee: Inovise Medical, Inc., Portland, OR (US)

( * ) Notice: Subject to any disclaimer, the term of this patent is extended or adjusted under 35 U.S.C. 154(b) by 473 days.

(21) Appl. No.: 10/461,732

(22) Filed: Jun. 13, 2003

(65) Prior Publication Data

US 2004/0254488 A1    Dec. 16, 2004

(51) Int. Cl.
*A61B 5/02* (2006.01)
*A61B 5/04* (2006.01)
*A61B 7/00* (2006.01)

(52) U.S. Cl. ............... 600/528; 600/513; 600/514; 600/586

(58) Field of Classification Search ........... 600/493, 600/513, 514, 528, 586; 128/901; 607/17, 607/18
See application file for complete search history.

(56) References Cited

U.S. PATENT DOCUMENTS 5,058,600 A * 10/1991 Schechter et al. ........ 600/529
6,168,568 B1 * 1/2001 Gavriely .................... 600/529
2002/0055684 A1 * 5/2002 Patterson ................... 600/528

* cited by examiner

*Primary Examiner*—Robert E. Pezzuto
*Assistant Examiner*—Tammie K. Heller
(74) *Attorney, Agent, or Firm*—Jon M. Dickinson PC; Robert D. Varitz PC

(57) ABSTRACT

A method and apparatus for gathering high-quality anatomical audio signals. Practice of the invention, which is illustrated herein in the context of heart-produced signals, is based upon gathering, and competitively processing audio signals collected simultaneously from two adjacent anatomical sites. Competitive processing examines these two signals in light of certain selected "quality" parameters, and thereby selects the better signal at a user-selected point in time.

7 Claims, 3 Drawing Sheets

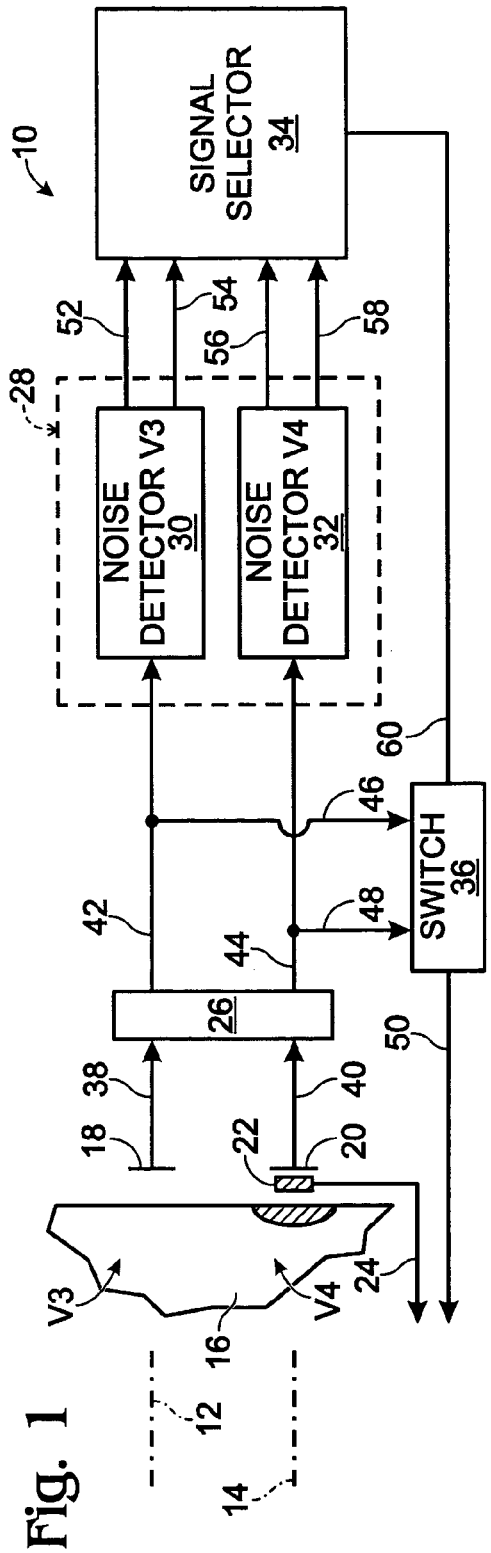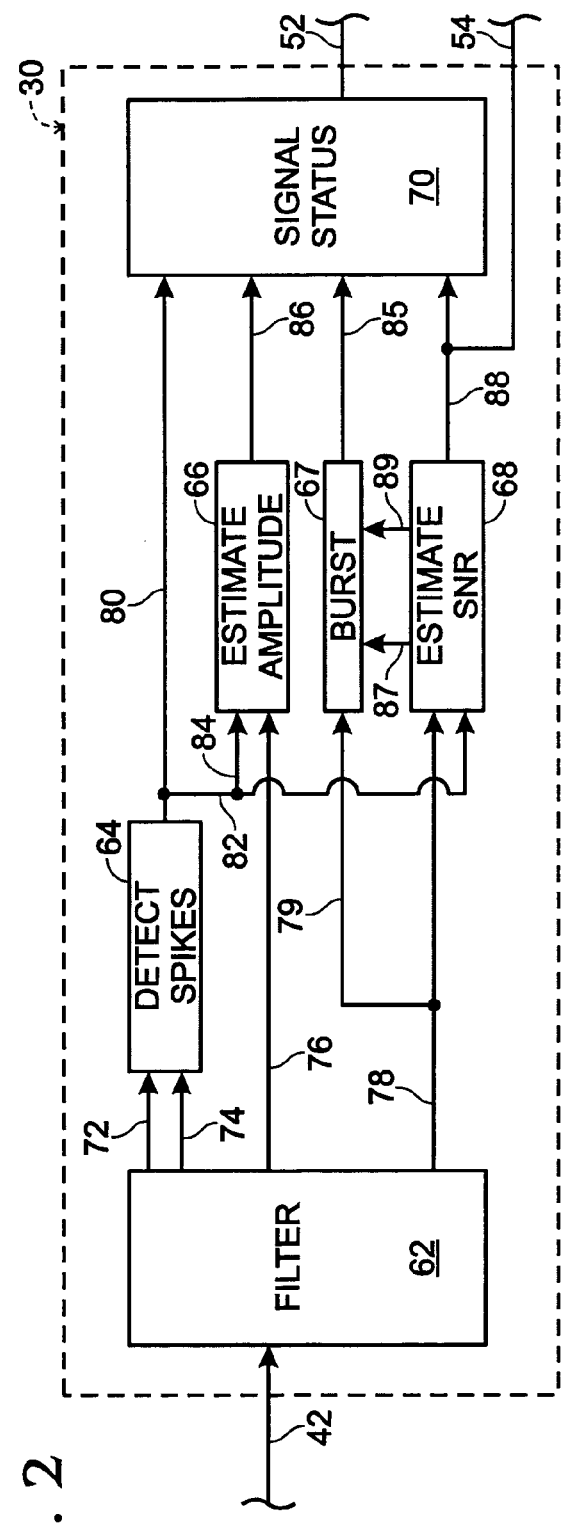

REAL-TIME, SOUND-QUALITY-COMPETITIVE, SINGLE-SITE FROM PLURAL-SITE, ANATOMICAL AUDIO SIGNAL SELECTION

BACKGROUND AND SUMMARY OF THE INVENTION

This invention pertains to a method and apparatus employed in the gathering, for observation purposes, of desired-category anatomical audio signal information effectively gathered from a specific, selected anatomical region, or site. In particular, it relates to such a method and apparatus which are capable of determining and selecting, from the mentioned selected anatomical site, and during a particular time interval, the highest-quality available audio signal, which signal may then be studied/reviewed in relation to selected anatomical electrical signals which are also present generally at the same site during the same time interval.

For the purpose of illustration herein, a preferred embodiment of, and manner of practicing, the present invention are described in the setting of collecting heart-produced audio signals from the traditional V4 ECG lead site on the anatomy for study along with ECG electrical signals collected essentially from the same site (as well as from other traditional ECG sites, if desired).

From a methodologic point of view, a preferred implementation of the present invention involves (a) the placement of a pair of audio sensors, or transducers, in close proximity to a selected anatomical site, such as the mentioned V4 lead site, (b) the gathering of simultaneously acquirable audio signals from those two sensors, (c) the competitive processing of such two signals in order to evaluate the higher-quality one of them in accordance with certain quality-selection parameters which are described below, and then (d) the selection and declaration of that higher-quality signal to be the chosen, desired-category audio output signal that may be reviewed along with a time-contemporaneous ECG signal derived also essentially directly from the V4 site.

As will be briefly mentioned below, one of the audio sensors, or transducers, or if desired, both such employed sensors, may be constructed in the form of a combined audio and electrical anatomical signal sensor of the type described in a currently co-pending U.S. patent application covering an invention entitled "Method and Apparatus for Detecting and Transmitting Electrical and Related Audio Signals From a Single, Common Anatomical Site, Ser. No. 10/389,402, filed Mar. 14, 2003. Reference is made to this currently co-pending patent application simply to provide background information relative to one manner of collecting an anatomical audio signal. Practice and utility of the present invention does not in any way depend upon specific features or behavioral capabilities of this representative structure.

The various features and advantages which are attained by the present invention will become more fully apparent as the description thereof which now follows is read in conjunction with the accompanying drawings.

DESCRIPTION OF THE DRAWINGS

FIG. 1 is a block/schematic diagram illustrating apparatus and a system constructed, and operating, in accordance with a preferred implementation of the present invention.

FIG. 2 is a block/schematic diagram illustrating, very generally, the internal construction of one (both being the same) of two noise detectors (part of signal processing structure) which are employed, one each for processing anatomical audio signals received from two, spaced audio transducers that are employed in accordance with practice of the invention.

DETAILED DESCRIPTION OF THE INVENTION

Figure 3:
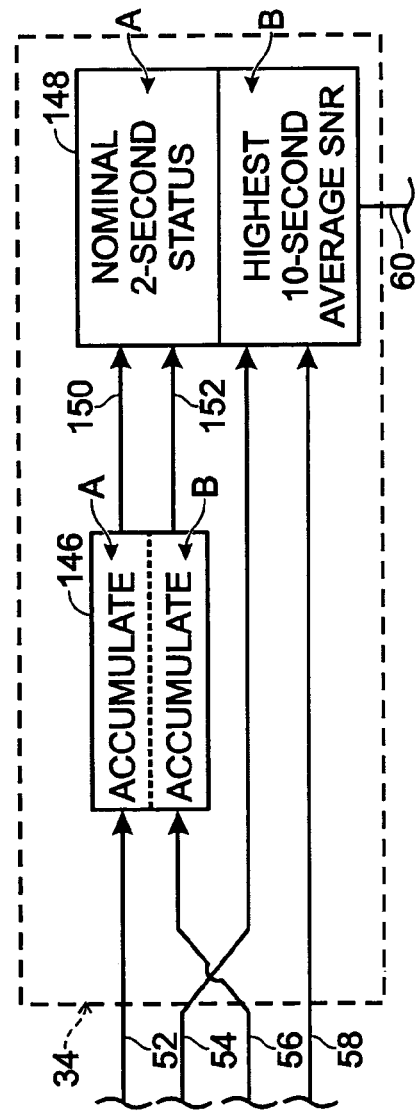
FIG. 3 is a block/schematic diagram further illustrating the construction of a block which is pictured in FIG. 1 labeled "SIGNAL SELECTOR".

Turning now to the drawings, recognizing that these drawings provide schematic structural (and functional) representations of the invention, and beginning first with FIG. 1, indicated generally at 10 is apparatus in the form of an operatively disposed system constructed to perform audio-signal gathering and selecting in accordance with practice of the present invention. Apparatus 10 is constructed, and performs, in accordance with a preferred and best mode embodiment and manner of practicing the invention. In FIG. 1, system/apparatus 10 is shown disposed to collect, along two "axes" shown generally at 12, 14, anatomical audio signal information from two conventionally known, relatively closely positioned, V3 and V4 ECG anatomical sites on a person's anatomy which is illustrated fragmentarily at 16. Site, or region, V4 herein is the region referred to as being the region of special selection, and system 10 is specifically illustrated in FIG. 1 in the context of gathering and selecting heart-produced sounds emanating essentially from this V4 region. While the V4 site is specifically discussed herein, other sites could also be selected.

The operative intention of system 10, as thus shown, is to gather, for observation purposes, as high a quality as possible "V4" heart sound in order to study and review this sound during a given, selected time interval, along with the simultaneously occurring ECG anatomical electrical signal also present at site V4. Such study and review is considered to be important in certain medical practices of interpreting heart behavior, and the gathering of a reliably informative V4 audio signal has sometimes been challenging when performed by various, conventional, prior-art techniques, essentially always employing a single audio sensor.

Sound-quality difficulties in the past, regarding the collection of heart-produced sounds, occur for a number of reasons, prevalent among which are: (1) nearfield audio signal effects; (2) the possibility of rib interposition in the intended sound-gathering path; (3) the poor quality of an "acoustic" seal between a gathering sensor (typically a microphone) and the surface of the anatomy; (4) the presence of intervening fat tissue; (5) competing gastrointestinal sounds; and others. These possible difficulties, and their respective severities, are often dramatically affected by the specific positioning and placement chosen for a sound sensor.

The present invention effectively addresses these issues by employing two audio sensors 18, 20 in FIG. 1, placed closely adjacent one another (within a few inches in close proximity to target site V4), and with audio signals gathered respectively thereby competitively processed, in accordance with certain quality-based parameters (discussed below), to select and declare the "higher-quality" sound as a designatable V4 audio sound. Sensors 18, 20 are also referred to herein as first and second audio signal sensors.

Sensors 18, 20 are each herein constructed as described in the mentioned copending U.S. patent application, wherein audio and electrical anatomical signal information is co-gathered along a substantially common axis which is positioned to intersect a single, specific, common anatomical site. Sensor 18 gathers audio information along previously mentioned axis 12 which is located near the V4 site, and specifically substantially at the conventional V3 site. Sensor 20, which is associated with an ECG, or electrical-signal, electrode 22, gathers audio information along previously mentioned axis 14, which extends through the conventional V4 anatomical site. Electrode 22 furnishes V4 ECG electrical signal information on a conductor 24.

Further included in system 10 are an analog-to-digital converter 26, a noise detection block 28 which includes two noise detectors 30, 32, a signal selector 34, and an electronic, digital selector switch 36. Two conductors 38, 40 feed analog electrical "sound" signals from sensors 18, 20, respectively, to the input side of converter 26, and associated conductors 42, 44, respectively, feed related digital output signals from the output side of converter 26 to the inputs, respectively, of noise detectors 30, 32. Branching conductors 46, 48 connect conductors 42, 44, respectively, to the input side of switch 36, whose single output is connected to a digital audio output conductor 50. Noise detectors 30, 32 which operate respectively on the digital versions of the analog signals coming from sensors 18, 20, along with signal selector 34, collaboratively perform what is referred to herein as competitive signal processing, and selection of the "higher-quality" one of the audio signals coming from the two audio sensors. Collectively they constitute signal processing structure in system 10.

Output signals from noise detectors 30, 32 are fed by pairs of conductors 52, 54 and 56, 58, respectively to the input side of signal selector 34. A conductor 60 connects the output side of the signal selector to the control input of switch 36. Conductor 60 is referred to herein as output structure, and it functions, according to the invention, to declare the selected, higher-quality audio signal.

With attention directed now to FIGS. 2 and 4 which specifically illustrate noise detector 30, included in this detector are a filter structure 62, a spike detector 64, an amplitude estimator 66, a burst noise detector 67 (referred to herein after as a burst detector), a signal-to-noise (SNR) estimator 68, and a signal status circuit 70. What constitutes "burst noise" is defined later herein.

Filter 62 is connected to spike detector 64 via conductors 72, 74, to amplitude estimator 66 via a conductor 76, to SNR estimator 68 by a conductor 78, and to burst detector 67 by conductor 78 and a conductor 79. The output of the spike detector feeds information to the signal status circuit, to the SNR estimator, and to the amplitude estimator by way of conductors 80, 82, 84, respectively. Signals sent from the spike detector over conductors 82, 84 to the SNR estimator and to the amplitude estimator, respectively, operate, on the occurrence of a spike being detected, to hold the outputs from these two estimators momentarily at their present values. This assures that no signal-quality declaration is made in the presence of an audio-spike event. The outputs of estimators 66, 68 supply information to signal status circuit 70 via conductors 86, 88, respectively. The output of burst detector 67 connects to circuit 70 via a conductor 85. Conductors 87, 89 interconnect the SNR estimator and the burst detector. Previously mentioned conductor 54 connects as shown with conductor 88.

Figure 4:
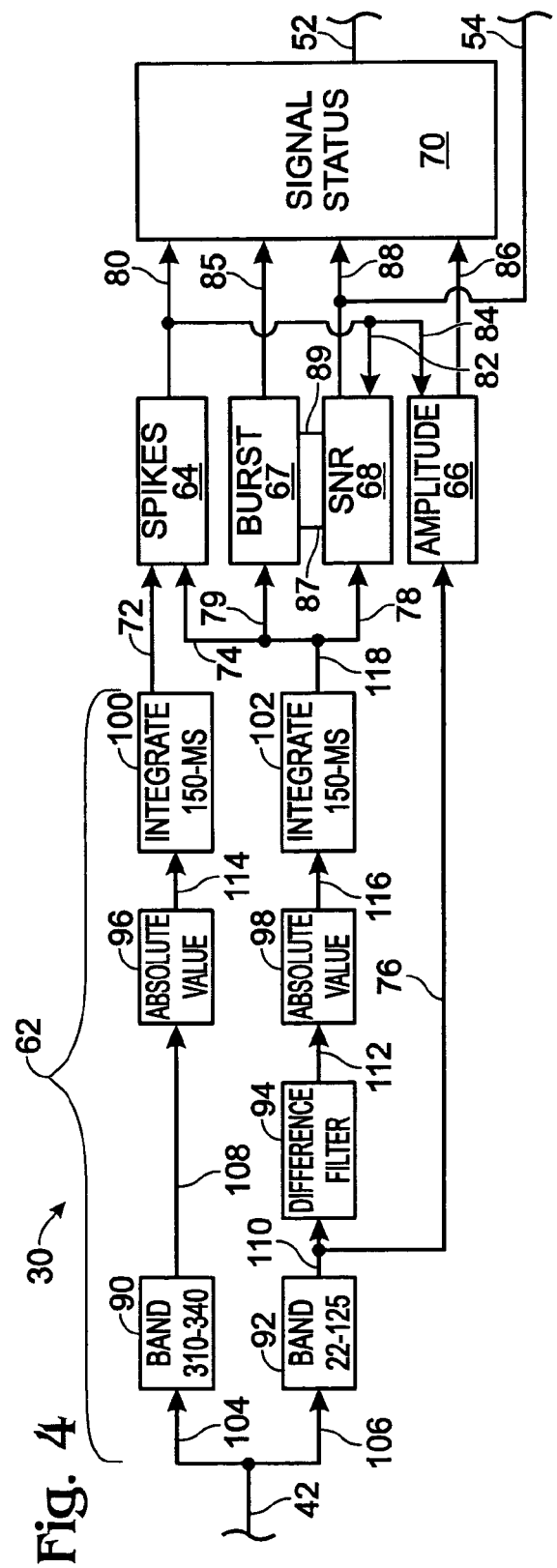
FIG. 4 is similar to FIG. 2, except that it illustrates in greater detail the structure found within a block pictured in FIG. 2 labeled "FILTER".

FIG. 4 illustrates that filter 62 includes two different-frequency-range band-pass filter blocks 90 (higher range, about 310–340-Hz), 92 (lower range, about 22–125-Hz), a difference filter 94, a pair of absolute value calculating blocks 96, 98, and two integrators 100, 102. These filter components are individually entirely conventional in construction. The passband of filter block 92, generally speaking, contains heart-produced sound frequencies of specified interest. Previously mentioned conductor 42 connects with the inputs to filter blocks 90, 92 via conductors 104, 106, respectively. The outputs of blocks 90, 92 feed information via conductors 108, 110, respectively, to conventional absolute value calculator 96, and to conventional difference filter 94. The difference filter connects with conventional absolute value calculator by way of conductor 112. Calculators 96, 98 connect through conductors 114, 116, respectively, with integrators 100, 102.

Within each of noise detectors 30, 32, effectively there is a comparison which is made of power that is present in signal information passing through each of the two band-pass (higher-frequency, lower-frequency) filters.

Completing a description of what appears in FIG. 4, previously mentioned conductor 72 extends between integrator 100 and spike detector 64. Integrator 102 connects with the spike detector, the SNR estimator, and the burst detector through a conductor 118, and previously mentioned conductors 74, 78, 79, respectively.

Figure 6:
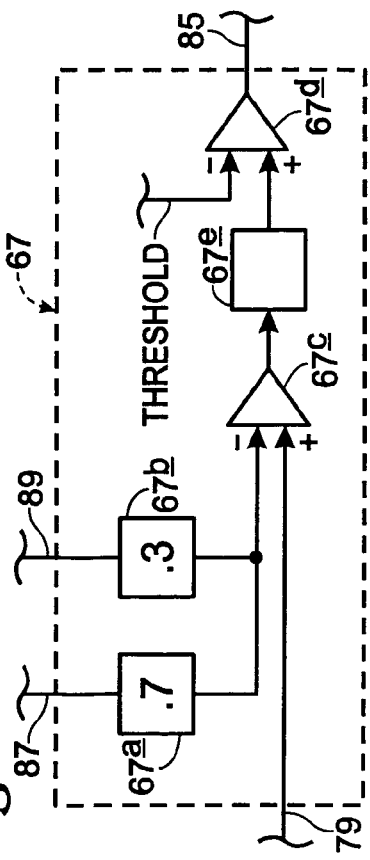
FIG. 6 is block/schematic diagram further illustrating a block which is labeled "BURST" in FIGS. 2 and 4.

FIG. 6 further illustrates burst detector 67. Burst detector 67 detects what has been referred to herein as burst noise. Such a noise is one which is characterized by an audio signal which lasts for more than about 300-milliseconds, and wherein the power level of the related audio signal, discernable effectively on conductor 118, is larger than the power level discernable effectively from the signal which is present on conductor 72. In other words, relevant to declaring an audio event as an indication of burst noise, that audio event is one which possesses only a modest amount of "high frequency" energy. This detector includes two multiply circuits 67a, 67b, two voltage comparators 67c, 67d, and a timer 67e, interconnected as shown. Circuits 67a, 67b which are connected to previously mentioned conductors 87, 89, respectively, apply multiplication factors of 0.7 and 0.3, respectively. This differential between multiplication factors indicates that information to the burst detector coming form the SNR estimator is treated in the burst detector with "weighting" given to information via conductor 87.

Figure 7:
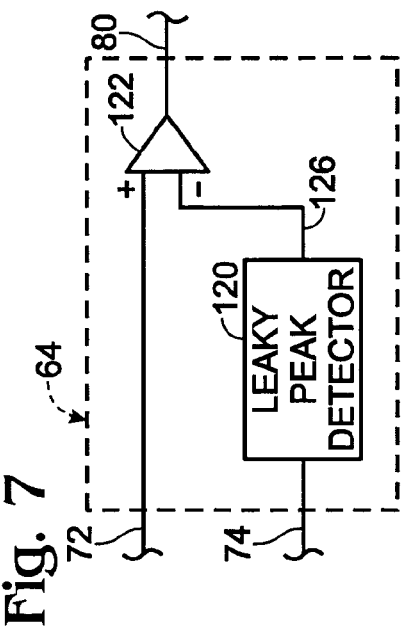
FIG. 7 is a block/schematic diagram further illustrating a block shown both in FIG. 2 and in FIG. 4 labeled "DETECT SPIKES" and "SPIKES", respectively.

FIG. 7 further illustrates spike detector 64, and shows that it includes a conventional leaky peak detector 120, and a conventional comparator 122. Conductors 72, 74 connect as shown to comparator 122 and to peak detector 120, respectively. A conductor 126 connects the output of the peak detector to comparator 122. The comparator output is connected to previously mentioned conductor 80.

Figure 8:
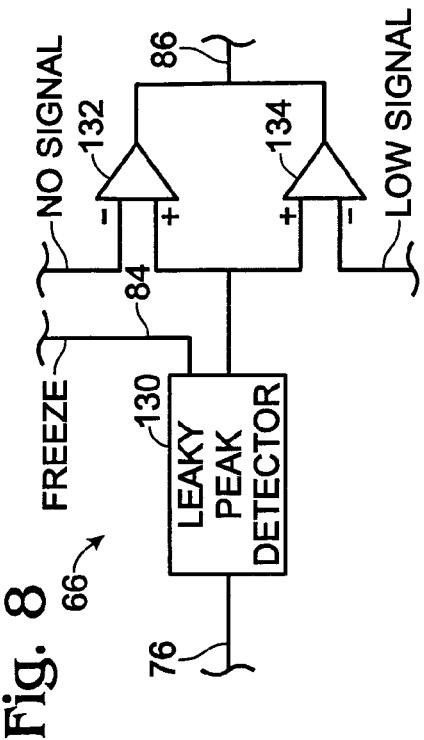
FIG. 8 is a block/schematic diagram illustrating a block in FIG. 2 which is labeled "ESTIMATE AMPLITUDE", which is the same block that is labeled "AMPLITUDE" in FIG. 4.

FIG. 8 shows the construction of amplitude estimator 66. Included here are another conventional leaky peak detector 130, and two conventional comparators 132, 134. The operative interconnections between these three amplitude estimator components are clearly presented in FIG. 8, as are the respective connections that exist between the amplitude estimator and previously described conductors 76, 84, 86.

Figure 5:
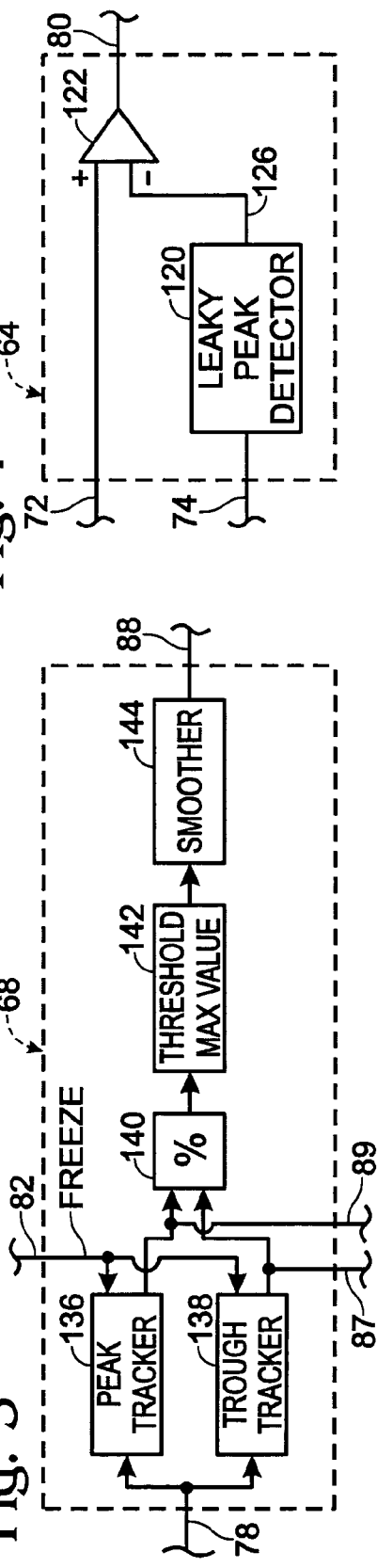
FIG. 5 is a block/schematic diagram further illustrating the internal makeup of a block pictured in FIG. 4 labeled "SNR". This same block is shown in FIG. 2, and is there labeled "ESTIMATE SNR".

FIG. 5 shows the preferred internal construction of SNR estimator 68. Included here are a conventional signal peak tracker 136, a conventional signal trough tracker 138, a conventional ratio circuit 140, a conventional maximum signal value threshold circuit 142, and a conventional signal smoother 144. The internal interconnections between these several components are clearly evident, as are the connections existing with previously discussed circuit conductors 78, 82, 87, 88, 89. Within SNR estimator 68, the outputs from peak and trough trackers 136, 138, respectively, are reflective of what is referred to herein as peak and trough signal-power information.

Finally with respect to what is shown in the drawings, FIG. 3 illustrates the make-up of signal selector 34, which is seen to include a "two-sided" (A, B) accumulator circuit 146, and a "two sided" (A, B) status assessment circuit 148. Previously mentioned conductors 52, 56 connect as shown with the inputs to sides A, B, respectively, in circuit 146. Conductors 54, 58 connect with the input to side B in assessment circuit 148. Two conductors 150, 152 connect sides A, B, respectively, in accumulator 146 to the input of side A in the assessment circuit. The output of the assessment circuit connects with previously mentioned conductor 60.

The respective natures of circuits 146, 148 will become apparent shortly from the operational description of the system of this invention.

Describing now the operation of the apparatus and methodology of the present invention, when it is to be placed in use, audio sensors 18, 20 are suitably applied to the anatomy close to one another, and close, typically, to conventional ECG site V4, as is pictured in FIG. 1. The thought behind this, as was mentioned earlier, is, effectively, to gather reliably useable audio signals essentially coming from the region of site V4. By utilizing two sensors for collecting audio information placed as described, this approach deals effectively with many of the sensor-placement issues described earlier. Operation of the invention, deriving, as it does, audio signal information from such two closely adjacent sites, is designed to "compete" the two gathered audio signals for the purpose of selecting, at different moments in time, and as appropriate, the higher-quality audio signal, which signal, ultimately, is to be reviewed along with ECG electrical data also effectively coming from selected site V4 (and perhaps from other sites also).

An electrode, such as electrode 22, is also properly positioned essentially at the V4 site. Where a combined audio and electrical sensor device, like the device illustrated and described in the mentioned co-pending patent application, is employed, that device is essentially disposed to gather both audio and anatomical electrical signals from the same anatomical site. However, as was also mentioned earlier, use of such a combined audio/electrical sensor is not a requirement involved in practice of the present invention.

When such anatomical positionings and attachments have been accomplished, the associated sensors and electrode begin monitoring audio and anatomical electrical signals.

With this activity under way, digital versions of the two collected audio signals which are developed by sensors 18, 20 are fed to the signal processing apparatus of the invention by way of analog-to-digital converter 26. From this converter, such signals are supplied to noise detection block 28. Specifically, the digital signal which is derived from sensor 18 goes to noise detector 30, and that derived from sensor 20 goes to noise detector 32. As will shortly be more fully explained, competitive processing which looks at a number of selected parameters takes place within these noise detectors ultimately to deliver to signal selector 34 two different pieces of information coming from each of the two noise detectors. One of these pieces of information possesses a level, or a value, which relates to what is referred to herein as a "nominal" signal status. This nominal signal status value is developed in each noise detector in light of parameters including (a) signal frequency, (b) signal amplitude, (c) signal power, and (d) the presence or absence of spike and/or burst noise. The other information supplied by each noise detector to the signal selector possesses a level, or a value, which is associated with signal-to-noise ratio (SNR). The first-mentioned piece of information is supplied with respect to approximately the last two-seconds of audio signal activity (at any moment in time). The signal-to-noise information piece relates, effectively, to the average SNR value over a preceding time interval of about ten-seconds.

Based upon the respective conditions of these pieces of information, as perceived by signal selector 34 at a point in time when a user is calling for the noting and recordation of audio information, the signal selector chooses which audio sensor will be the then-declared source of the desired, higher-quality audio signal to be supplied by switch 36 to output conductor 50. As will shortly be seen, the first-level evaluation is performed with respect to a comparison of the two "nominal" signal status values coming from the two noise detectors. If one of these values is more prevalent than the other, the signal selector chooses whichever audio signal is related to that more-prevalent nominal status. If the nominal status values supplied by the two noise detectors match one another, then a second-level determination selects that source of audio information which, in the prior interval of about ten-seconds, has produced an average signal-to-noise ratio which is the higher one of the two such SNR values.

Looking now at the operation which takes place in each of the two noise detectors, and describing this in relation to fully illustrated noise detector 30, and now making reference especially to FIGS. 2 and 4, the audio signal in digital form coming into this noise detector is fed in parallel to the two band-pass filters which, in turn, feed respective output signals to the two different "chains" of processing blocks illustrated clearly downstream from these filters in FIG. 4. Those skilled in the art will understand the operations taking place within these blocks given the fact that they are each internally conventional in construction.

The various outputs (three in number, on conductors 72, 76, 118) coming from filtration activities are supplied, as shown, to the spike detector, to the burst detector, to the SNR estimator, and to the amplitude estimator, as pictured. Effectively, the immediate downstream strings of processing blocks and conductors provided for the two band-pass filters furnish output information that is related to signal amplitude, and to signal power and frequency present in the outputs of the two frequency passbands.

Output signals from the upper band-pass filter are processed in block 96 to create and absolute value signal level which is then integrated in block 100 over a period of 150-milliseconds to provide a signal that is fed via conductor 72 to one input in spike detector 64. Signals flowing from the output of the lower band-pass filter are first processed by difference filter 94, and then handled by block 98 to create another absolute value signal level which is also integrated, in this case by block 102, over a period of 150-milliseconds. Output from integrator block 102 is furnished, as shown, to inputs in spike detector 64, in burst detector 67, and in SNR estimator 68. All of this information, along with the direct supply to the amplitude estimator of the output signal from the output of the lower frequency band-pass filter, is then treated within blocks 64, 66, 67 and 68, to create appropriate, related output signals that are provided to signal status block 70.

The following text now generally describes what takes place with respect to the operations of blocks 64, 66, 67, 68 and 70.

Burst detector 67 (see FIG. 6) takes a weighted average of the peak tracker (136) and trough tracker (138) outputs from SNR estimator 68, and uses that as a threshold. When the 150-milliseconds integral (performed in block 102) of the 22–125-Hz power is above this threshold, timer 67e counts up. This produces an estimate of the duration of the heart sounds. If a sound lasts longer than about 350-milliseconds, a burst is detected (the output of the burst detector goes to a binary one). When the power falls below the threshold, the timer is reset.

The output of the signal status block 70 is determined, as has been mentioned, by incoming signals from spike detector 64, from burst detector 67, from amplitude estimator 66, and from the SNR estimator 68.

If the output of the amplitude estimator is zero (indicating amplitude below the NO SIGNAL threshold), then the signal status output is NO SIGNAL. If the output of the amplitude estimator is 1 (indicating amplitude below the LOW SIGNAL threshold, but above the NO SIGNAL threshold), then the signal status output is LOW SIGNAL. If the output of the SNR estimator is below a predetermined threshold (e.g. 1.9), then the signal status is CONTINUOUS NOISE. If the output of the spike detector is 1 (indicating that a spike is detected), then the signal status output is SPIKE NOISE. If the output of the burst detector is 1, then the signal status output is BURST NOISE. If none of the above conditions occurs, then the signal status output is NOMINAL.

These six possible output values just mentioned are encoded internally as integer values from 0 to 5.

The output of SNR estimator 68 as pictured herein (see FIG. 5) lies in the range 0–12.

For every sample of data, the signal status block (70) produces an output as described above. Sides A,B in accumulate-circuit 146 accumulate these outputs over a two-second period, and each "side" produces an output which changes no more often than every two-seconds. The output from each accumulate-circuit side represents certain characteristics of the signal quality of the associated source audio signal over the previous two-seconds.

As has been indicated earlier, there is one accumulate-circuit side for each of the two audio sensors. Inputs to the each accumulate-circuit side come from the associated signal status block. The output from each of these sides is determined as follows:

> If at least 50% of the inputs over two-seconds are NOMINAL, and less than 50-milliseconds of the inputs over two-seconds are BURST NOISE
>     output = NOMINAL
> If any of the inputs over two-seconds is NO SIGNAL
>     output = NO SIGNAL
> If any of the inputs over two-seconds is LOW SIGNAL
>     output = LOW SIGNAL
> If any of the inputs over two-seconds is BURST NOISE
>     output = BURST NOISE -continued > If any of the inputs over two-seconds is SPIKE NOISE
>     output = SPIKE NOISE
> If any of the inputs over two-seconds is CONTINUOUS NOISE)
>     output = CONTINUOUS NOISE The decision-making (declaring) operation of assessment circuit 148 is as follows:

If one accumulate-circuit side has more NOMINAL outputs than does the other within the last ten-seconds, circuit 148 picks, as the declared, higher-quality audio signal, the audio signal which is associated with that one side. If that is not the case, i.e., if both "sides" show an equal number of NOMINAL outputs, then circuit 148 picks the audio side with the highest SNR, as averaged over the preceding ten-seconds.

There is thus provided by this invention a novel method and novel apparatus for acquiring high-quality audio information from a selected anatomical site. A key feature involves the simultaneous gathering/collecting of audio signals by two independent, closely adjacent audio sensors which are placed on the anatomy near that site. This dual-collection practice, coupled with appropriate competitive signal processing to apply certain quality-assessment parameters as described, results in the reliable, useful acquisition of an anatomical audio signal to be reviewed confidently along with related electrical (such as ECG) signal information.

While a preferred and best mode embodiment of, and manner of practicing, the invention have been illustrated and described herein, variations and modifications may be made without departing from the spirit of the invention.

We claim:

1. A method employed in the gathering, for observation purposes, of desired-category anatomical audio signal information effectively from a selected anatomical region, said method comprising
    placing first and second audio signal sensors/detectors on the anatomy at selected locations of adjacency relative to such region,
    gathering, and competitively processing, the respective audio signals detected by these two sensors for the purpose of selecting, during a given, defined time-frame, one of these two detected signals as the higher-quality signal as such is determined by the review of certain pre-chosen quality-selection parameters, and
    declaring such selected higher-quality audio signal to be the one containing the desired-category audio signal information from the selected anatomical region during the defined time-frame.

2. The method of claim 1 which further includes the simultaneous collecting of anatomical electrical signal information, and said declaring is performed, at least in part, for the purpose of enabling the study of a selected relationship of such collected electrical signal information with the declared, desired-category audio signal information.

3. The method of claim 2, wherein said collecting of electrical signal information is performed by the collecting of EGG signal information.

4. The method of claim 1, wherein said competitive processing includes, for each of the two gathered audio signals, comparing, during the defined time-frame, signal power present in two different signal-frequency bands, one of which is a higher-frequency band, and other of which is a lower-frequency band, and utilizing this power comparison as an indication of the presence of spike noise.

5. The method of claim 4, wherein said competitive processing further includes, in relation to the presence of spike noise, and during the defined time-frame, noting, and then utilizing, selected peak and trough signal-power information present in the mentioned lower-frequency band to create a related signal-to-noise ratio estimate which is associated with the determined absence of spike noise.

6. The method of claim 5, wherein said competitive processing further includes, in relation to the presence of spike noise, and during the defined time-frame, performing a signal amplitude estimation related to signal information contained in the mentioned lower-frequency band during a determined condition of the absence of spike noise, and then employing collaboratively (a) information regarding the presence/absence of spike noise, (b) information relating to the created signal-to-noise ratio estimate, and (c) the mentioned signal amplitude estimation as operative quality-selection parameters, to perform the step of declaring the selected higher-quality audio signal.

7. The method of claim 5, wherein said competitive processing further includes examining audio information to detect burst noise.

* * * * *